United States Patent
Schulze zur Wiesche et al.

(10) Patent No.: US 9,421,160 B2
(45) Date of Patent: *Aug. 23, 2016

(54) METHOD FOR CHEMICAL SMOOTHING OF HUMAN HAIRS

(71) Applicant: Henkel AG & Co. KGaA, Duesseldorf (DE)

(72) Inventors: Erik Schulze zur Wiesche, Hamburg (DE); Stephan Schwartz, Wedel (DE); Birgit Rautenberg-Groth, Ellerau (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/570,027

(22) Filed: Dec. 15, 2014

(65) Prior Publication Data

US 2015/0096585 A1    Apr. 9, 2015

Related U.S. Application Data

(63) Continuation of application No. PCT/EP2013/059982, filed on May 15, 2013.

(30) Foreign Application Priority Data

Jun. 29, 2012  (DE) .......................... 10 2012 211 266

(51) Int. Cl.

| | |
|---|---|
| *A61Q 5/04* | (2006.01) |
| *A61K 8/898* | (2006.01) |
| *A61K 8/43* | (2006.01) |
| *A45D 7/06* | (2006.01) |

(52) U.S. Cl.
CPC . *A61K 8/898* (2013.01); *A45D 7/06* (2013.01); *A61K 8/43* (2013.01); *A61Q 5/04* (2013.01); *A61K 2800/24* (2013.01); *A61K 2800/884* (2013.01)

(58) Field of Classification Search
None
See application file for complete search history.

(56) References Cited

U.S. PATENT DOCUMENTS

| | | | |
|---|---|---|---|
| 4,324,263 A | 4/1982 | de la Guardia | |
| 8,894,984 B2* | 11/2014 | Schulze zur Wiesche | C08G 77/26 424/489 |
| 8,900,329 B2* | 12/2014 | Schulze zur Wiesche | C08G 77/26 424/70.1 |
| 8,900,561 B2* | 12/2014 | Schulze zur Wiesche | A61Q 5/12 424/489 |
| 9,005,593 B2* | 4/2015 | Dutheil-Gouret | A61K 8/731 424/70.12 |
| 9,066,892 B2* | 6/2015 | Schulze zur Wiesche | A61Q 5/004 |
| 2003/0115685 A1 | 6/2003 | Devin-Baudoin et al. | |
| 2003/0118537 A1* | 6/2003 | Devin-Baudoin | A61K 8/898 424/70.2 |
| 2012/0114584 A1 | 5/2012 | Woghiren et al. | |

FOREIGN PATENT DOCUMENTS

JP          2-250814 A      10/1990

OTHER PUBLICATIONS

PCT International Search Report (PCT/EP2013/059982) dated May 14, 2014.

* cited by examiner

*Primary Examiner* — Jyothsna Venkat
(74) *Attorney, Agent, or Firm* — David K. Benson

(57) ABSTRACT

A method for reshaping, in particular for straightening, keratin-containing fibers, in particular human hair, includes (i) applying a pretreatment agent including amino-functional silicone(s) with terminal hydroxyl group(s) onto the keratinic fibers and left there, (ii) optionally drying fibers, (iii) treating the fibers in the moist or dried state with a reshaping agent which, relative to the weight of the reshaping agent, includes 0.05 to 20 wt. % of guanidine and/or guanidinium salt(s), (iv) optionally straightening the fibers with a comb or a brush during the reshaping treatment, (v) shampooing the fibers with a shampoo which has a pH of 2.5 to 6.5, followed by rinsing and neutralizing the fibers, and (vi) optionally subsequently additionally mechanically deforming the fibers with exposure to heat. The methods distinctly minimizes the negative consequences of reshaping, in particular electrostatic charging and hydrophilization of the hair.

8 Claims, No Drawings

METHOD FOR CHEMICAL SMOOTHING OF HUMAN HAIRS

FIELD OF THE INVENTION

The present invention generally relates to the technical field of reshaping keratin-containing fibers, in particular human hair. The present invention provides an improved method for reshaping keratin-containing fibers, in particular human hair. Keratin-containing fibers which may be used are in principle all kinds of animal hair, for example wool, horsehair, angora hair, furs, feathers and products or textiles manufactured therefrom. However, the invention is preferably used for the purpose of reshaping hair, in particular straightening frizzy human hair and wigs made therefrom.

BACKGROUND OF THE INVENTION

Durable deformation of keratin-containing fibers is conventionally carried out in that the fibers are deformed mechanically and the deformation is set by suitable aids. The fibers are treated with a keratin-reducing preparation before and/or after this shaping. After a rinsing process, the fibers are then treated in the "setting step" with an oxidizing agent preparation and rinsed and the deformation aids (for example curlers or foam rollers) are removed after or during the setting step. If a mercaptan, for example ammonium thioglycolate, is used as the keratin-reducing component, this breaks down some of the disulfide bridges of the keratin molecule into —SH groups, such that the keratin fibers are softened. In the case of subsequent oxidative setting, disulfide bridges are relinked in the hair keratin, such that the keratin structure is set in the predetermined deformation. Alternatively it is known to use sulfite instead of mercaptans for hair deformation. Hydrogensulfite solutions and/or sulfite solutions and/or disulfite solutions break down disulfide bridges of the keratin in a sulfitolysis reaction according to the equation

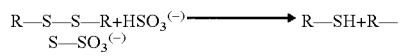

and in this way the keratin fibers are softened. Hydrogensulfite, sulfite or disulfite-containing reducing agents do not have the strong intrinsic odor of the mercaptan-containing agents. As described above, breakdown can be reversed in a setting step, with the assistance of an oxidizing agent, so forming new disulfide bridges.

Permanent straightening of keratin-containing fibers is achieved in a similar manner by the use of keratin-reducing and keratin-oxidizing compositions. In a corresponding method, the frizzy hair is either wound on curlers with a large diameter of conventionally more than 15 mm or the hair is combed straight while being exposed to the keratin-reducing composition. Instead of the curler, it is also possible to lay the fibers flat onto a straightening board. Straightening boards are conventionally rectangular boards of plastics, for example. The fibers are then preferably wetted with the keratin-reducing preparation.

In general, the known reshaping processes, in particular in the case of straightening, have the disadvantage that the keratin-containing fibers become electrostatically charged. Furthermore, the treatment with reshaping agent increases the hydrophilicity of the hair, which makes it more difficult to style and impairs handle, combability and gloss.

It is therefore desirable to provide a reshaping method for keratin-containing fibers, in particular for human hair, which produces a very good, durable reshaping result and at the same time minimizes electrostatic charging and hydrophilization of the hair, cares for the fibers and is gentle on the structure of the fibers.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

A method for reshaping, in particular for straightening, keratin-containing fibers, in particular human hair, includes the step of applying a pretreatment agent including amino-functional silicone(s) with terminal hydroxyl group(s) onto the keratinic fibers; the fibers are optionally dried; the fibers are treated in the moist or dried state with a reshaping agent which, relative to the weight of the reshaping agent, includes 0.05 to 20 wt. % of guanidine and/or guanidinium salt(s); the fibers are optionally straightened with a comb or a brush during the reshaping treatment; the fibers are shampooed with a shampoo which has a pH of 2.5 to 6.5, rinsed and neutralized; and the fibers are optionally subsequently additionally mechanically deformed with exposure to heat.

A method for reducing or preventing hair damage due to a chemical hair straightening treatment may be characterized such that, before the chemical hair treatment, a pretreatment agent including amino-functional silicone(s) with terminal hydroxyl group(s) is applied onto the keratinic fibers.

A method for producing a washing-resistant conditioning action before a chemical hair straightening treatment may be characterized such that, before the chemical hair treatment, a pretreatment agent including amino-functional silicone(s) with terminal hydroxyl group(s) is applied onto the keratinic fibers.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

It has surprisingly been found that pretreatment of the fibers with specific pretreatment agents distinctly minimizes the negative consequences of reshaping and in particular minimizes electrostatic charging and hydrophilization of the hair. By using reshaping agents specifically designed for pretreatment, the reshaping result is also distinctly improved.

The present invention provides in a first embodiment a method for reshaping, in particular for straightening, keratin-containing fibers, in particular human hair, in which (i) a pretreatment agent including amino-functional silicone(s) with terminal hydroxyl group(s) is applied onto the keratinic fibers and left there, (ii) the fibers are optionally dried, (iii) the fibers are treated in the moist or dried state with a reshaping agent which, relative to the weight of the reshaping agent, includes 0.05 to 20 wt. % of guanidine and/or guanidinium salt(s), (iv) the fibers are optionally straightened with a comb or a brush during the reshaping treatment, (v) the fibers are shampooed with a shampoo which has a pH of 2.5 to 6.5, rinsed and neutralized, (vi) the fibers are optionally subsequently additionally mechanically deformed with exposure to heat.

In the method according to the invention, a pretreatment agent including amino-functional silicone(s) with terminal hydroxyl group(s) is firstly applied to the keratinic fibers and left there.

The pretreatment agent applied in step (i) is not rinsed out, but rather remains on the fibers. The fibers can be optionally dried in step (ii), which may occur by air drying in the case of extended exposure times to the pretreatment agent. With shorter application times, the hair may for example be rubbed with a hand towel. After completion of the rubbing step, the hair remains perceptibly damp.

The pretreatment agents used in the method according to the invention include amino-functional silicone(s) with terminal hydroxyl group(s). Such silicones may, for example, be described by the formula

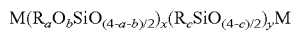

$$M(R_aQ_bSiO_{(4-a-b)/2})_x(R_cSiO_{(4-c)/2})_yM$$

wherein in the above formula R is a hydrocarbon or a hydrocarbon residue with 1 to approximately 6 carbon atoms, Q is a polar residue of the general formula —$R^1$HZ, in which $R^1$ is a divalent linking group, which is attached to hydrogen and the residue Z, composed of carbon and hydrogen atoms, carbon, hydrogen and oxygen atoms or carbon, hydrogen and nitrogen atoms, and Z is an organic, amino-functional residue, which includes at least one amino-functional group; "a" assumes values in the range from approximately 0 to approximately 2, "b" assumes values in the range from approximately 1 to approximately 3, "a"+"b" is less than or equal to 3, and "c" is a number in the range from approximately 1 to approximately 3, and x is a number in the range from 1 to approximately 2000, preferably from approximately 3 to approximately 50 and most preferably from approximately 3 to approximately 25, and y is a number in the range from approximately 20 to approximately 10000, preferably from approximately 125 to approximately 10000 and most preferably from approximately 150 to approximately 1000, and M is a suitable silicone end group with hydroxyl function, preferably hydroxy-dimethylsiloxy. Non-limiting examples of the residues represented by R include alkyl residues, such as methyl, ethyl, propyl, isopropyl, isopropyl, butyl, isobutyl, amyl, isoamyl, hexyl, isohexyl and the like; alkenyl residues, such as vinyl, halovinyl, alkylvinyl, allyl, haloallyl, alkylallyl; cycloalkyl residues, such as cyclobutyl, cyclopentyl, cyclohexyl and the like; phenyl residues, benzyl residues, halogenated hydrocarbon residues, such as 3-chloropropyl, 4-bromobutyl, 3,3,3-trifluoropropyl, chlorocyclohexyl, bromophenyl, chlorophenyl and the like and sulfur-containing residues, such as mercaptoethyl, mercaptopropyl, mercaptohexyl, mercaptophenyl and the like; R is preferably an alkyl residue, which includes 1 to approximately 6 carbon atoms, and most preferably R is methyl. Examples of $R^1$ include methylene, ethylene, propylene, hexamethylene, decamethylene, —$CH_2CH(CH_3)CH_2$—, phenylene, naphthylene, —$CH_2CH_2SCH_2CH_2$—, —$CH_2CH_2OCH_2$—, —$OCH_2CH_2$—, —$OCH_2CH_2CH_2$—, —$CH_2CH(CH_3)C(O)OCH_2$—, —$(CH_2)_3CC(O)OCH_2CH_2$—, —$C_6H_4C_6H_4$—, —$C_6H_4CH_2C_6H_4$—; and —$(CH_2)_3C(O)SCH_2CH_2$—.

Z is an organic, amino-functional residue including at least one functional amino group. A possible formula for Z is $NH(CH_2)_zNH_2$, in which z is 1 or more. Another possible formula for Z is —$NH(CH_2)_z(CH_2)_{zz}NH$, in which both z and zz are mutually independently 1 or more, wherein this structure comprises diamino ring structures, such as piperazinyl. Z is most preferably an —$NHCH_2CH_2NH_2$ residue. Another possible formula for Z is —$N(CH_2)_z(CH_2)_{zz}NX_2$ or —$NX_2$, in which each X of $X_2$ is independently selected from the group consisting of hydrogen and alkyl groups with 1 to 12 carbon atoms, and zz is 0.

Q is most preferably a polar amino-functional residue of formula —$CH_2CH_2CH_2NHCH_2CH_2NH_2$. In the formulae, "a" assumes values in the range from approximately 0 to approximately 2, "b" assumes values in the range from approximately 2 to approximately 3, "a"+"b" is less than or equal to 3, and "c" is a number in the range from approximately 1 to approximately 3. The molar ratio of the $R_aQ_bSiO_{(4-a-b)/2}$ units to the $R_cSiO_{(4-c)/2}$ units is in the range from approximately 1:2 to 1:65, preferably from approximately 1:5 to approximately 1:65 and most preferably from approximately 1:15 to approximately 1:20. If one or more silicones of the above formula are used, then the various variable substituents in the above formula may be different in the various silicone components which are present in the silicone mixture.

In methods according to the invention amino-functional silicones of formula (Si-II) may be used, for example:

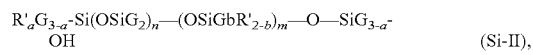

in which:
G is —H, a phenyl group, —OH, —O—$CH_3$, —$CH_3$, —O—$CH_2CH_3$, —$CH_2CH_3$, —O—$CH_2CH_2CH_3$, —$CH_2CH_2CH_3$, —O—$CH(CH_3)_2$, —$CH(CH_3)_2$, —O—$CH_2CH_2CH_2CH_3$, —$CH_2CH_2CH_2CH_3$, —O—$CH_2CH(CH_3)_2$, —$CH_2CH(CH_3)_2$, —O—$CH(CH_3)CH_2CH_3$, —$CH(CH_3)CH_2CH_3$, —O—$C(CH_3)_3$, —$C(CH_3)_3$;
a denotes a number between 0 and 3, in particular 0;
b denotes a number between 0 and 1, in particular 1,
m and n are numbers, the sum of which (m+n) amounts to between 1 and 2000, preferably between 50 and 150, wherein n preferably assumes values from 0 to 1999 and in particular from 49 to 149 and m preferably assumes values from 1 to 2000, in particular from 1 to 10,
R' is a monovalent residue selected from
-Q-N(R")—$CH_2$—$CH_2$—N(R")$_2$
-Q-N(R")$_2$
-Q-$N^+$(R")$_3A^-$
-Q-$N^+$H(R")$_2A^-$
-Q-$N^+H_2$(R")$A^-$
-Q-N(R")—$CH_2$—$CH_2$—$N^+R''H_2A^-$,
wherein each Q denotes a chemical bond, —$CH_2$—, —$CH_2$—$CH_2$—, —$CH_2CH_2CH_2$—, —$C(CH_3)_2$—, —$CH_2CH_2CH_2CH_2$—, —$CH_2C(CH_3)_2$—, —CH($CH_3$)$CH_2CH_2$—,
R" denotes identical or different residues from the group —H, phenyl, benzyl, —$CH_2$—$CH(CH_3)$Ph, $C_{1-20}$ alkyl residues, preferably —$CH_3$, —$CH_2CH_3$, —$CH_2CH_2CH_3$, —$CH(CH_3)_2$, —$CH_2CH_2CH_3$, —$CH_2CH(CH_3)_2$, —$CH(CH_3)CH_2CH_3$, —$C(CH_3)_3$, and A represents an anion which is preferably selected from chloride, bromide, iodide or methosulfate.

In methods according to the invention of this embodiment, amino-functional silicones of formula (Si-IIa) may preferably be used:

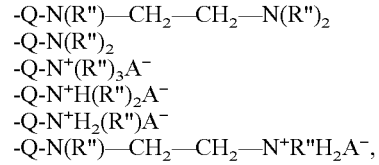

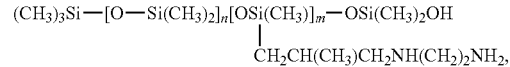

in which m and n are numbers, the sum of which (m+n) amounts to between 1 and 2000, preferably between 50 and 150, wherein n preferably assumes values from 0 to 1999 and in particular from 49 to 149 and m preferably assumes values from 1 to 2000, in particular from 1 to 10.

Agents according to the invention which are more preferred are also those which include an amino-functional silicone of formula (Si-IIb)

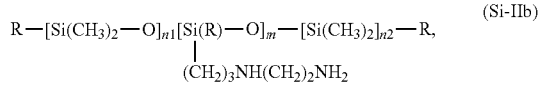

(Si-IIb)

in which R denotes —OH, —O—$CH_3$ or a —$CH_3$ group and m, n1 and n2 are numbers the sum of which (m+n1+n2) amounts to between 1 and 2000, preferably between 50 and 150, wherein the sum (n1+n2) preferably assumes values from 0 to 1999 and in particular from 49 to 149 and m preferably assumes values from 1 to 2000, in particular from 1 to 10. According to the invention, at least one R here denotes —OH.

These silicones are denoted in accordance with the INCI Declaration as Amodimethicones.

Irrespective of which amino-functional silicones are used, preferred agents according to the invention are those which include an amino-functional silicone, the amine value of which is above 0.25 meq/g, preferably above 0.3 meq/g and in particular above 0.4 meq/g. The amine value here denotes the milliequivalents of amine per gram of the amino-functional silicone. It can be determined by titration and may also be stated in the unit mg of KOH/g.

The input quantity of the amino-functional silicone(s) with terminal hydroxyl group(s) in the pretreatment agent used in the method according to the invention may vary, preferred methods being characterized in that the pretreatment agent includes, relative to the weight thereof, 0.00001 to 10 wt. %, preferably 0.0001 to 7.5 wt. %, more preferably 0.001 to 5 wt. %, still more preferably 0.01 to 2.5 wt. % and in particular 0.1 to 1 wt. % amino-functional silicone(s) with terminal hydroxyl group(s).

Some specific amino-functional silicone(s) with terminal hydroxyl group(s) have proven particularly suitable in the method according to the invention. These are described below.

Methods preferred according to the invention are characterized in that in step (i) a pretreatment agent is applied which, relative to the weight thereof, includes 0.01 to 5 wt. %, preferably 0.025 to 2.5 wt. %, further preferably 0.05 to 1.5 wt. %, still more preferably 0.075 to 1 wt. % and in particular 0.1 to 0.25 wt. % of at least one silicone of formula (I)

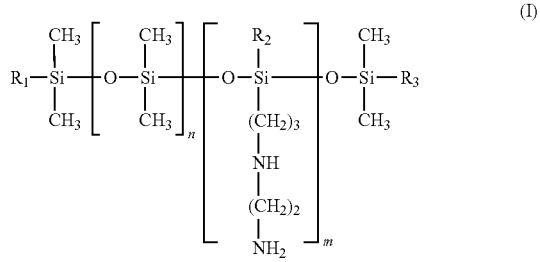

(I)

in which
m and n mean numbers which are selected such that the sum (n+m) is in the range from 1 to 1000,
n is a number in the range from 0 to 999 and m is a number in the range from 1 to 1000,
$R_1$, $R_2$ and $R_3$, which are identical or different, mean a hydroxyl group or a $C_{1-4}$ alkoxy group,
wherein at least one of groups $R_1$ to $R_3$ means a hydroxyl group.

Further methods preferred according to the invention are characterized in that in step (i) a pretreatment agent is applied which, relative to the weight thereof, includes 0.01 to 5 wt. %, preferably 0.025 to 2.5 wt. %, further preferably 0.05 to 1.5 wt. %, still more preferably 0.075 to 1 wt. % and in particular 0.1 to 0.25 wt. % of at least one silicone of formula (II)

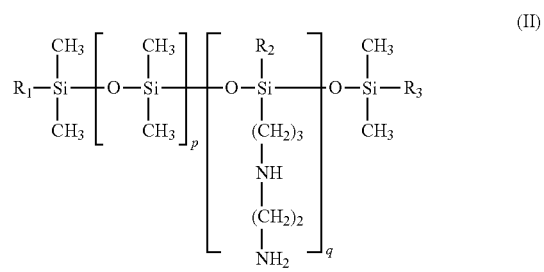

(II)

in which
p and q mean numbers which are selected such that the sum (p+q) is in the range from 1 to 1000,
p is a number in the range from 0 to 999 and q is a number in the range from 1 to 1000,
$R_1$ and $R_2$, which are different, mean a hydroxyl group or a $C_{1-4}$ alkoxy group, wherein at least one of groups $R_1$ to $R_2$ means a hydroxyl group.

The silicones of formulae (I) and (II) differ in the grouping on the Si atom which bears the nitrogenous group: in formula (I) $R^2$ denotes a hydroxyl group, or a $C_{1-4}$ alkoxy group, while the residue in formula (II) is a methyl group. The individual Si groupings, which are identified with the indices m and n or p and q, need not be present as blocks, but rather the individual units may also be randomly distributed, i.e. in the formulae (I) and (II) each $R^1$—$Si(CH_3)_2$ group is not necessarily attached to an —[O—$Si(CH_3)_2$] grouping.

In the method according to the invention, pretreatment agents which have proven particularly effective with regard to the desired effects are those which include at least one silicone of formula (III):

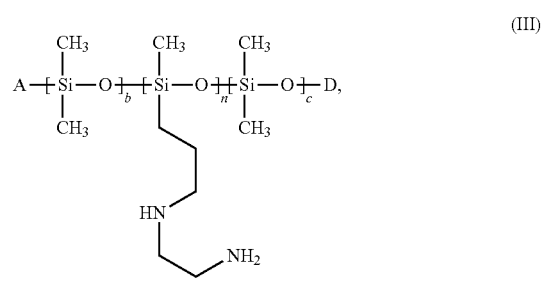

(III)

in which
A denotes a group —OH, —O—$Si(CH_3)_3$, —O—Si$(CH_3)_2$OH or —O—Si$(CH_3)_2$O$CH_3$,
D denotes a group —H, —Si$(CH_3)_3$, —Si$(CH_3)_2$OH or —Si$(CH_3)_2$O$CH_3$, b, n and c denote integers between 0 and 1000, with the provisos n>0 and b+c>0 at least one of the conditions A=—OH or D=—H is met.

Methods according to the invention in which in step (i) a pretreatment agent is applied which, relative to the weight thereof, includes 0.01 to 5 wt. %, preferably 0.025 to 2.5 wt. %, further preferably 0.05 to 1.5 wt. %, still more preferably 0.075 to 1 wt. % and in particular 0.1 to 0.25 wt. % of at least one silicone of formula (III):

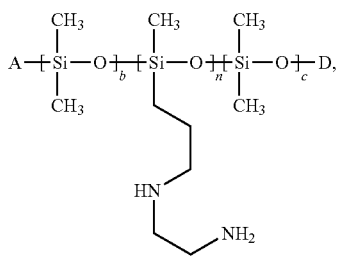

(III)

in which

A denotes a group —OH, —O—Si(CH$_3$)$_3$, —O—Si(CH$_3$)$_2$OH or —O—Si(CH$_3$)$_2$OCH$_3$, D denotes a group —H, —Si(CH$_3$)$_3$, —Si(CH$_3$)$_2$OH or —Si(CH$_3$)$_2$OCH$_3$, b, n and c denote integers between 0 and 1000, with the provisos n>0 and b+c>0 at least one of the conditions A=—OH or D=—H is met, are accordingly preferred according to the invention.

In the above-stated formula (III) the individual siloxane units with the indices b, c and n are randomly distributed, i.e. they need not necessarily be block copolymers.

Further particularly suitable silicones are 4-morpholinomethyl-substituted. Methods according to the invention, in which the a pretreatment agent, relative to the weight thereof, includes 0.01 to 5 wt. %, preferably 0.025 to 2.5 wt. %, more preferably 0.05 to 1.5 wt. %, still more preferably 0.075 to 1 wt. % and in particular 0.1 to 0.25 wt. % of at least one 4-morpholinomethyl-substituted silicone of formula (IV),

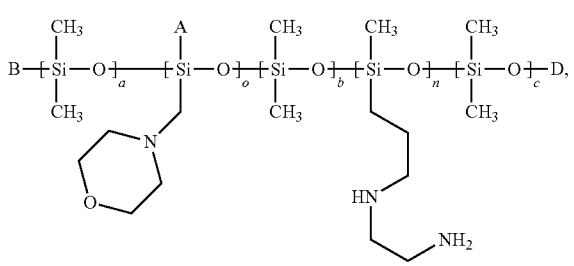

(IV)

in which

A denotes a structural unit (i), (ii) or (iii) attached via an —O—

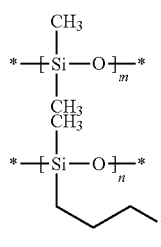

(i)

(ii)

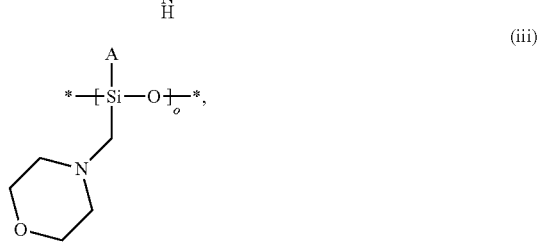

(iii)

or denotes an oligomeric or polymeric residue attached via an —O— and including structural units of formulae (I), (II) or (III) or half of a bonded O atom to a structural unit (iii) or denotes —OH,

* denotes a bond to one of structural units (i), (ii) or (iii) or denotes an end group B (Si-bound) or D (O-bound), B denotes a group —OH, —O—Si(CH$_3$)$_3$, —O—Si(CH$_3$)$_2$OH or —O—Si(CH$_3$)$_2$OCH$_3$, D denotes a group —H, —Si(CH$_3$)$_3$, —Si(CH$_3$)$_2$OH or —Si(CH$_3$)$_2$OCH$_3$, a, b and c denote integers between 0 and 1000, with the proviso a+b+c>0 m, n and o denote integers between 1 and 1000, with the proviso that at least one of the conditions B=—OH or D=—H is met, are more preferred.

Structural formula (IV) is intended to clarify that the siloxane groups n and o need not necessarily be directly attached to an end grouping B or D. Instead, in preferred formulae (IV) a>0 or b>0 and in more preferred formulae (IV) a>0 and b>0, i.e. the terminal grouping B or D is preferably attached to a dimethylsiloxane grouping. In formula (IV) too, the siloxane units a, b, c, n and o are preferably randomly distributed.

The silicones used according to the invention and represented by formula (IV) may be trimethylsilyl-terminated (D or B=—Si(CH$_3$)$_3$), but they may also be dimethylsilylhydroxy-terminated at both ends or dimethylsilylhydroxy-terminated at one end and dimethylsilylmethoxy-terminated at the other. For the purposes of the present invention, silicones which are more preferably used are selected from silicones in which B=—O—Si(CH$_3$)$_2$OH and D=—Si(CH$_3$)$_3$ B=—O—Si(CH$_3$)$_2$OH and D=—Si(CH$_3$)$_2$OH B=—O—Si(CH$_3$)$_2$OH and D=—Si(CH$_3$)$_2$OCH$_3$ B=—O—Si(CH$_3$)$_3$ and D=—Si(CH$_3$)$_2$OH B=—O—Si(CH$_3$)$_2$OCH$_3$ and D=—Si(CH$_3$)$_2$OH.

These silicones lead to enormous improvements in the properties of the hair treated with the agents according to the invention, in particular to greatly improved protection during oxidative treatment.

In formula (IV) too, the residue A may denote a structural unit (i), (ii) or (iii) attached via an —O— or an oligomeric or polymeric residue attached via an —O— and including structural units of formulae (i), (ii) or (iii) or half of a bonded O atom to a structural unit (iii) or it may denote —OH.

Thus, formula (IV) is narrowed to one of formulae (IVa), (IVb), (IVc), (IVd), (IVe) or (IVf):
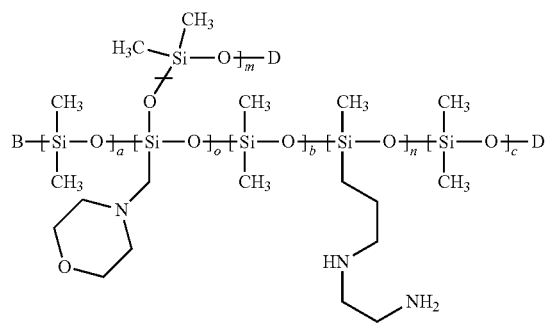
(IVa)
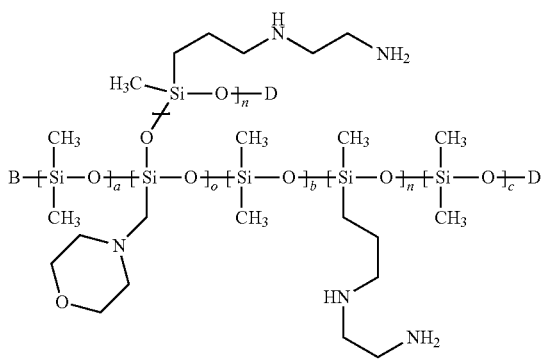
(IVb)
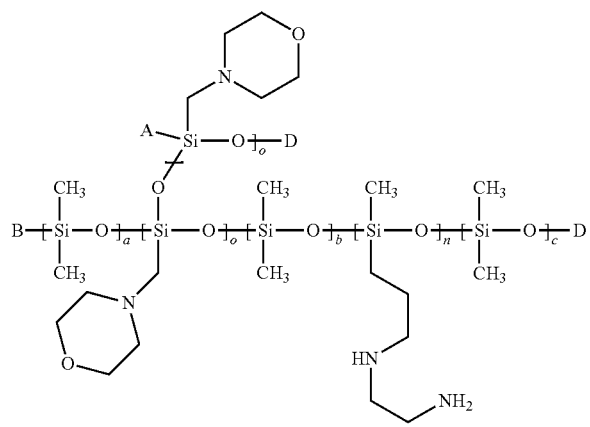
(IVc)
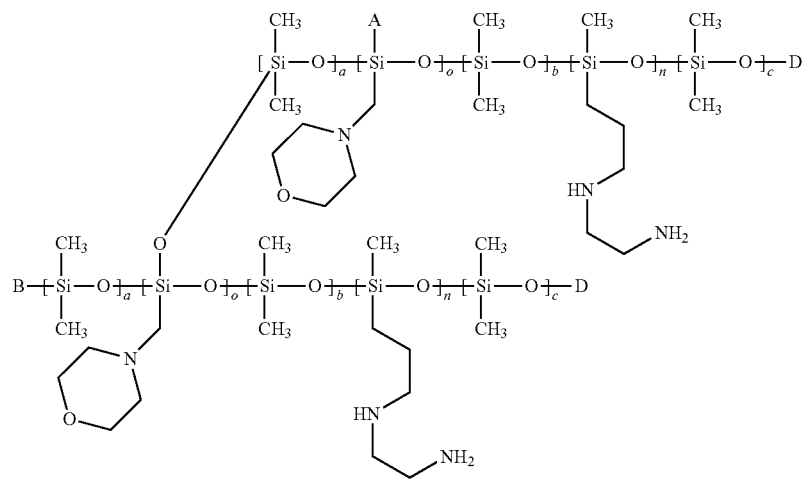
(IVd)

(IVe)

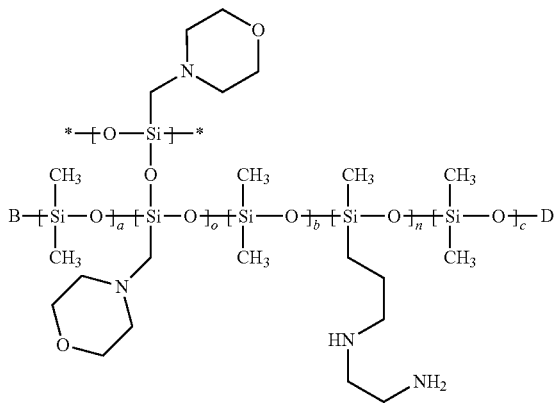

(IVf)

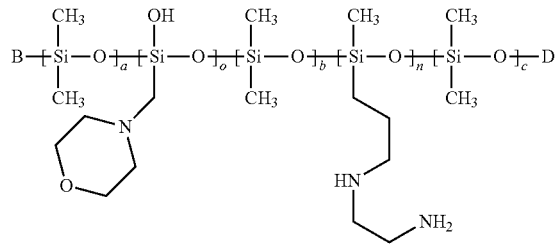

The structural unit (iii) or the siloxane units o in the formulae (IV) may form nest or partial cage structures via group A, if A denotes half of a bonded O atom to a structural unit (iii). Pretreatment agents according to the invention, which include silicones with corresponding 4-morpholinomethyl-substituted silsesquioxane substructures, are preferred according to the invention, since these silicones enormously improve hair protection against oxidative treatment.

It is more preferred in methods according to the invention of the above-stated embodiment for the pretreatment agent to contain, relative to the weight thereof, 0.00001 to 10 wt. %, preferably 0.0001 to 7.5 wt. %, more preferably 0.001 to 5 wt. %, more preferably 0.01 to 3 wt. % and in particular 0.1 to 1 wt. % of 4-morpholinomethyl-substituted silicone(s).

Irrespective of the type of amino-functional silicone(s) used with terminal hydroxyl group(s), the pretreatment agents used in the method according to the invention include the silicone(s) preferably in the form of an emulsion, more preferably in the form of a microemulsion. Microemulsions which have proven more preferable are those which include fatty alcohols as emulsifiers or stabilizers, such that preferred methods according to the invention are characterized in that the pretreatment agent assumes the form of a microemulsion including fatty alcohol(s).

It has been found that the action of the silicones used in the pretreatment agents for the purpose of the method according to the invention may be further enhanced if specific nonionic components are likewise used in the pretreatment agents. These nonionic components furthermore have positive effects on the storage stability of the pretreatment agents. Nonionic components which are particularly suitable here are ethoxylates of decanol, undecanol, dodecanol, tridecanol etc. Ethoxylated tridecanols have proven particularly suitable and are more preferentially incorporated into the pretreatment agents used in the method according to the invention. More preferred methods according to the invention are characterized in that the pretreatment agent, relative to the weight thereof, includes 0.00001 to 5 wt. %, preferably 0.0001 to 3.5 wt. %, more preferably 0.001 to 2 wt. %, further preferably 0.01 to 1 wt. % and in particular 0.1 to 0.5 wt. % of branched, ethoxylated tridecanol (INCI name: Trideceth-5) or α-iso-tridecyl-ω-hydroxy polyglycol ether (INCI name: Trideceth-10) or mixtures thereof.

The pretreatment agents used in the method according to the invention may moreover include further conventional ingredients of cosmetic agents.

As already mentioned, the fibers may optionally be dried in step (ii), which may proceed by air drying in the case of extended exposure times to the pretreatment agent. With shorter application times, the hair may for example be rubbed with a hand towel. After completion of the rubbing step, the hair remains perceptibly damp. Preferred methods according to the invention are characterized in that the fibers are dried in step (ii).

In the next step (iii) of the method according to the invention, a reshaping auxiliary is applied to the fibers. According to the invention, the reshaping agent includes, relative to the weight thereof, 0.05 to 20 wt. % of guanidine and/or guanidinium salt(s). In addition to guanidine $NH_2$—$C(=NH)NH_2$, guanidinium salts from the group guanidinium chloride, guanidinium thiocyanate and guanidinium nitrate have proven particularly successful. It is particularly preferred according to the invention to use guanidinium carbonate, such that extremely preferred methods according to the invention are characterized in that the fibers are treated in step (iii) with a reshaping agent which, relative to the weight of the reshaping agent, includes 0.05 to 20 wt. %, preferably 0.1 to 15 wt. %, further preferably 0.25 to 10 wt. %, still more preferably 0.5 to 5 wt. %, more preferably 0.75 to 3 wt. % and in particular 1 to 2 wt. % of guanidinium carbonate.

It is still more preferable to use guanidinium carbonate as the sole component from the group of guanidine and/or guanidinium salt(s), i.e. not mixed with guanidine and/or other guanidinium salts.

The excellent reshaping effectiveness of guanidinium carbonate can be still further increased it is mixed directly before use with alkali metal hydroxide(s). In this manner, elevated reshaping effectiveness is combined with the gentlest possible fiber treatment. Methods which are preferred according to the invention are therefore characterized in that the reshaping agent is freshly prepared immediately (no longer than 30 min) before use by mixing a component A and component B, wherein component A includes guanidine carbonate and component B includes alkali metal hydroxide(s).

A particularly preferred reshaping agent in this method variant is one which is freshly prepared immediately (no longer than 30 min) before use by mixing a component A and component B, wherein component A, relative to the weight thereof, includes 0.05 to 10 wt. %, preferably 0.1 to 7.5 wt. %, further preferably 0.25 to 5 wt. %, still more preferably 0.5 to 4 wt. %, more preferably 0.75 to 3 wt. % and in particular 1 to 2 wt. % of guanidine carbonate and component B, relative to the weight thereof, includes 0.05 to 10 wt. %, preferably 0.1 to 7.5 wt. %, further preferably 0.25 to 5 wt. %, still more preferably 0.5 to 4 wt. %, more preferably 0.75 to 3 wt. % and in particular 1 to 2 wt. % of sodium hydroxide.

In this particularly preferred method variant, a mixing ratio of components A and B to one another of 2:1 to 1:2, preferably of 3:2 to 2:3 and in particular of 1:1 is in turn more preferred.

During exposure to the reshaping agent, the fibers may be mechanically treated, in particular combed or brushed. Methods which are preferred according to the invention include a step (iv) in which the fibers are straightened with a comb or a brush during the reshaping treatment.

The two agents applied to the keratinic fibers in step (i) (pretreatment agent) and (iii) (reshaping agent) are removed from the fibers in step (v) of the method according to the invention by the fibers being shampooed with a shampoo with a pH of from 2.5 to 6.5, rinsed and neutralized. This slightly acidic treatment lowers the pH value back down from the level of approx. 8-11 reached during use of the reshaping agent. Corresponding neutralizing shampoos with pH values of between 2.5 and 6.5, preferably of between 5.5 and 6.5, may include all the conventional ingredients of hair cleansing agents.

Methods preferred according to the invention are additionally characterized in that the shampoo used in treatment step (v) includes phenolsulfonphthalein as pH indicator.

Irrespective of whether the hair has been straightened in step (iv) of the method according to the invention using a comb or a brush, reshaping of the keratin fibers may be assisted by a further method step. This mechanical deformation subsequent to shampooing may proceed in step (vi) of the method according to the invention, wherein the reshaping may optionally be assisted by heat, for example by heated curlers or, more preferably, by using hair straighteners.

Methods according to the invention in which the fibers are subjected in step (vi) to heat treatment at a temperature of 50° C. to 350° C. (preferably 80° C. to 280° C., more preferably 100° C. to 250° C., further preferably 140° C. to 220° C.) are preferred according to the invention.

The present invention also provides a method for reducing or preventing hair damage due to a chemical hair straightening treatment, in which, before the chemical hair treatment, a pretreatment agent including amino-functional silicone(s) with terminal hydroxyl group(s) is applied onto the keratinic fibers.

The present invention also provides a method for producing a washing-resistant conditioning action before a chemical hair straightening treatment, in which, before the chemical hair treatment, a pretreatment agent including amino-functional silicone(s) with terminal hydroxyl group(s) is applied onto the keratinic fibers.

The above statements regarding the first-stated method according to the invention apply mutatis mutandis to preferred embodiments of the latter two methods according to the invention.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A method for reshaping and/or straightening keratin-containing fibers, comprising:
   (i) applying a pretreatment agent including, relative to the weight thereof, 0.01 to 5 wt. % amino-functional silicone(s) with terminal hydroxyl group(s) onto the keratinic fibers,
   (ii) drying the fibers,
   (iii) treating the fibers in the dried state with a reshaping agent that, relative to the weight of the reshaping agent, includes 0.05 to 20 wt. % of guanidine and/or guanidinium salt(s),
   (iv) straightening the fibers with a comb or a brush during the reshaping treatment,
   (v) shampooing the fibers with a shampoo which has a pH of 2.5 to 6.5, followed by rinsing and neutralizing the fibers, and
   (vi) optionally subsequently mechanically deforming the fibers with exposure to heat, wherein the amino-functional silicone(s) is/are selected from the group consisting of formulas (I), (II), (III), and (IV):
   formula (I) being as follows

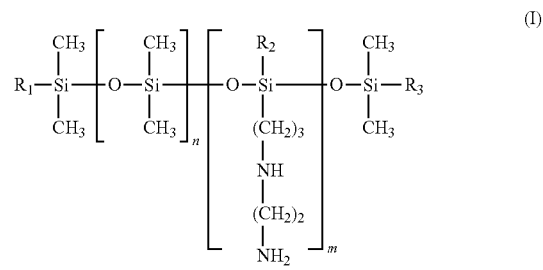

in which
   m and n are numbers which are selected such that the sum (n+m) is in the range from 1 to 1000,
   n is a number in the range from 0 to 999 and m is a number in the range from 1 to 1000,
   $R_1$, $R_2$ and $R_3$, which are identical or different, are either a hydroxyl group or a $C_{1-4}$ alkoxy group,
   wherein at least one of groups $R_1$ to $R_3$ is a hydroxyl group;
formula (II) being as follows

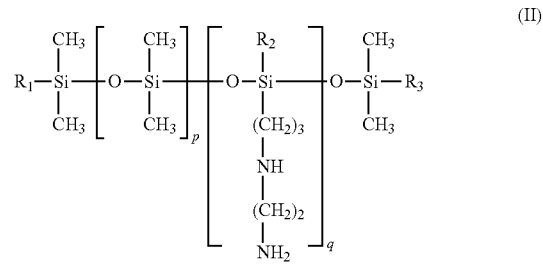

in which
   p and q are numbers which are selected such that the sum (p+q) is in the range from 1 to 1000,
   p is a number in the range from 0 to 999 and q is a number in the range from 1 to 1000, $R_1$ and $R_2$, which are different, are each a hydroxyl group or a $C_{1-4}$ alkoxy group, wherein at least one of groups $R_1$ to $R_2$ is a hydroxyl group;

formula (III) being as follows

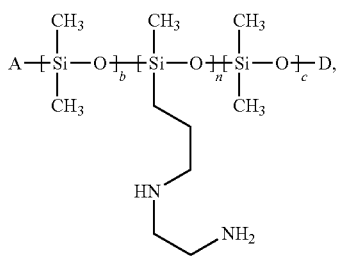
(III)

in which

A denotes a group —OH, —O—Si(CH$_3$)$_3$, —O—Si(CH$_3$)$_2$OH or —O—Si(CH$_3$)$_2$OCH$_3$, D denotes a group —H, —Si(CH$_3$)$_3$, —Si(CH$_3$)$_2$OH or —Si(CH$_3$)$_2$OCH$_3$, b, n and c each denote integers between 0 and 1000, with the provisos n>0 and b+c>0, and at least one of the conditions A=—OH or D=—H is met; and formula (IV) being at least one 4-morpholinomethyl-substituted silicone as follows

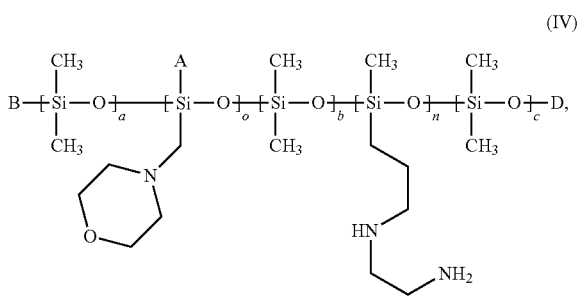
(IV)

in which

A denotes a structural unit (i), (ii) or (iii) attached via an —O—

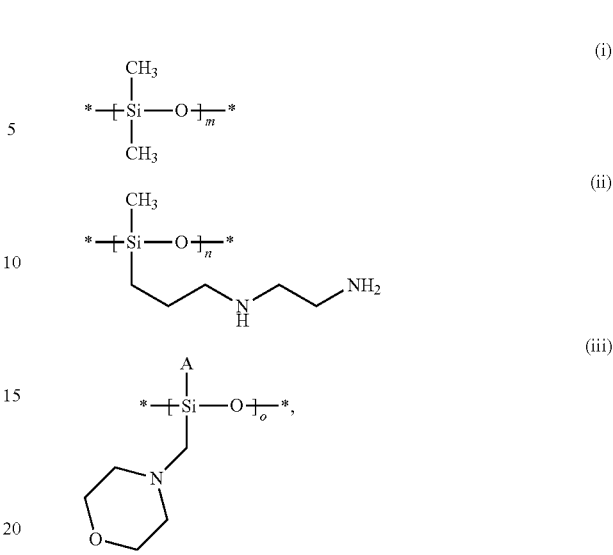
(i)
(ii)
(iii)

or denotes an oligomeric or polymeric residue attached via an —O— and including structural units of formulae (I), (II) or (III) or half of a bonded O atom to a structural unit (iii) or denotes —OH,

* denotes a bond to one of structural units (i), (ii) or (iii) or denotes an end group B (Si-bound) or D (O-bound), B denotes a group —OH, —O—Si(CH$_3$)$_3$, —O—Si(CH$_3$)$_2$OH or —O—Si(CH$_3$)$_2$OCH$_3$, D denotes a group —H, —Si(CH$_3$)$_3$, —Si(CH$_3$)$_2$OH or —Si(CH$_3$)$_2$OCH$_3$, a, b and c each denote integers between 0 and 1000, with the proviso a+b+c>0 m, n and o each denote integers between 1 and 1000, with the proviso that at least one of the conditions B=—OH or D=—H is met.

2. The method according to claim 1, characterized in that in step (i) the pretreatment agent includes at least one 4-morpholinomethyl-substituted silicone selected from the group consisting of formulae (IVa), (IVb), (IVc), (IVd), (IVe) and (IVf)

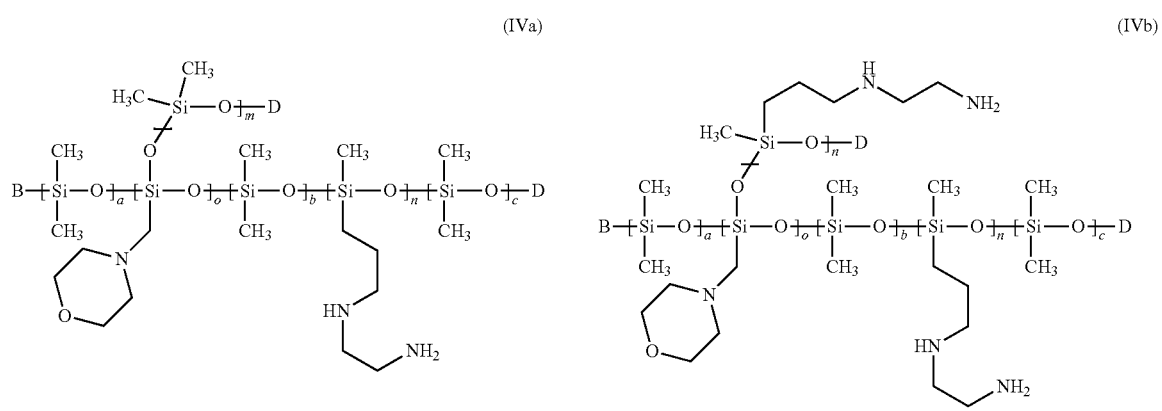
(IVa) (IVb)

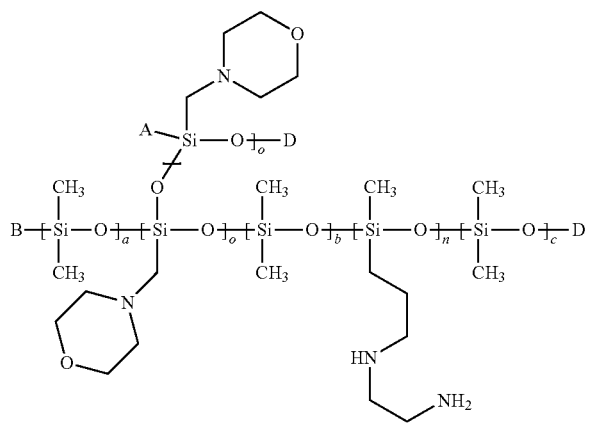

(IVc)

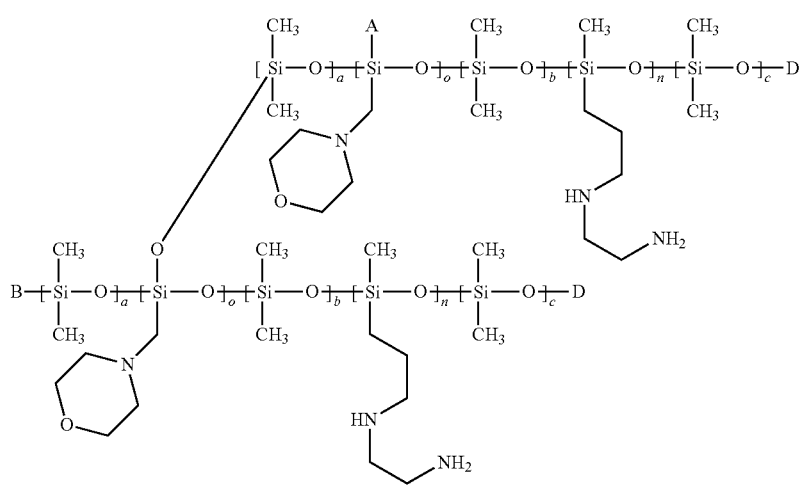

(IVd)

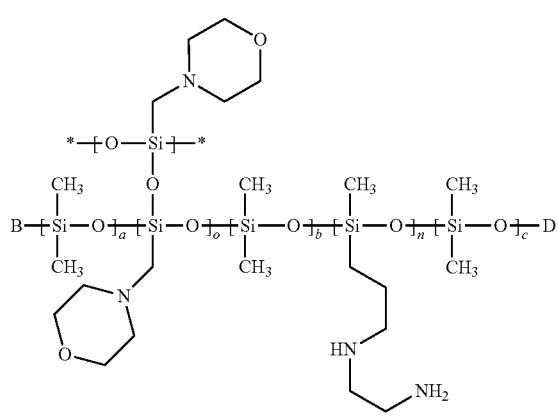

(IVe)

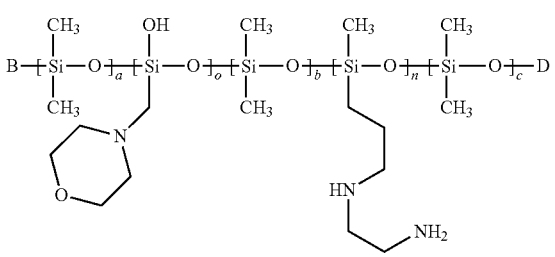

(IVf)

in which
B denotes a group —OH, —O—Si(CH$_3$)$_3$, —O—Si(CH$_3$)$_2$OH or —O—Si(CH$_3$)$_2$OCH$_3$,
D denotes a group —H, —Si(CH$_3$)$_3$, —Si(CH$_3$)$_2$OH or —Si(CH$_3$)$_2$OCH$_3$,
a, b and c each denote integers between 0 and 1000, with the proviso a+b+c>0
m, n and o each denote integers between 1 and 1000,
with the proviso that at least one of the conditions B=—OH or D=—H is met.

3. The method according to claim 1, characterized in that in step (i) the pretreatment agent is applied which assumes the form of a microemulsion which includes fatty alcohol(s).

4. The method according to claim 1, characterized in that in step (i) the pretreatment agent is applied which, relative to the weight thereof, includes 0.00001 to 5 wt. % of Trideceth-5 or Trideceth-10 or mixtures thereof.

5. The method according to claim 1, characterized in that the reshaping agent is freshly prepared no longer than 30 min before use by mixing a component A and component B, wherein component A includes guanidine carbonate and component B includes alkali metal hydroxide(s).

6. The method according to claim 5, characterized in that the fibers are treated in step (iii) with the reshaping agent which, relative to the weight of the reshaping agent, includes 0.05 to 20 wt. % of the guanidine carbonate.

7. The method according to claim 1, characterized in that the shampoo in treatment step (v) includes phenolsulfonphthalein as pH indicator.

8. The method according to claim 1, characterized in that the fibers are subjected in step (v) to a heat treatment at a temperature of 50° C. to 350° C.

\* \* \* \* \*